(12) United States Patent
Murrells et al.

(10) Patent No.: US 7,219,556 B2
(45) Date of Patent: May 22, 2007

(54) YARN SNARLING TESTING APPARATUS AND METHOD

(75) Inventors: Charlotte Murrells, Kowloon (HK);
Ka-Kee Wong, Kowloon (HK);
Xiaoming Tao, Kowloon (HK);
Bingang Xu, Kowloon (HK)

(73) Assignee: The Hong Kong Polytechnic University, Hong Kong SAR (CN)

( * ) Notice: Subject to any disclaimer, the term of this patent is extended or adjusted under 35 U.S.C. 154(b) by 232 days.

(21) Appl. No.: 10/996,611

(22) Filed: Nov. 26, 2004

(65) Prior Publication Data

US 2006/0144122 A1    Jul. 6, 2006

(51) Int. Cl.
*G01N 19/02* (2006.01)

(52) U.S. Cl. .............. 73/828; 73/159; 73/160; 73/788; 73/789; 73/826; 73/827

(58) Field of Classification Search .......... 73/828, 73/159, 160, 826, 827, 788, 789
See application file for complete search history.

(56) References Cited

U.S. PATENT DOCUMENTS

| | | | | |
|---|---|---|---|---|
| 2,706,909 | A | * | 4/1955 | Boor .................... 73/159 |
| 3,037,162 | A | * | 5/1962 | Jones et al. .......... 324/558 |
| 3,063,007 | A | * | 11/1962 | Baugh et al. ........ 324/558 |
| 3,076,251 | A | * | 2/1963 | Barber .................. 28/232 |
| 3,107,523 | A | * | 10/1963 | Oliver, Jr. et al. ...... 73/860 |
| 3,141,328 | A | * | 7/1964 | Weiner et al. .......... 73/159 |
| 3,726,137 | A | * | 4/1973 | Denton ................. 73/160 |
| 3,762,220 | A | * | 10/1973 | Gusack et al. ......... 73/160 |
| 3,899,927 | A | * | 8/1975 | Brassard et al. ....... 73/160 |
| 4,057,350 | A | * | 11/1977 | Craig .................. 356/429 |
| 5,167,150 | A | * | 12/1992 | Shofner et al. ........ 73/160 |
| 5,203,206 | A | * | 4/1993 | Shofner et al. ........ 73/160 |
| 5,799,103 | A | * | 8/1998 | Schneider et al. ..... 382/141 |
| 5,966,918 | A | * | 10/1999 | Kino et al. ............. 57/264 |
| 6,513,748 | B2 | * | 2/2003 | Zeller et al. ........ 242/419.1 |
| 6,701,704 | B2 | * | 3/2004 | Foster et al. ........... 57/333 |
| 7,020,940 | B2 | * | 4/2006 | Foster ................... 28/271 |

OTHER PUBLICATIONS

Dhingra et al, Jour of Textile Institute, vol. 65, 1974, pp. 126 133, The Measurement of Torque in Continuous-Filament Yarns.

(Continued)

*Primary Examiner*—Edward Lefkowitz
*Assistant Examiner*—Freddie Kirkland, III
(74) *Attorney, Agent, or Firm*—Jacobson Holman PLLC

(57) ABSTRACT

A process for measuring snarling properties of a yarn is provided. Firstly a first and a second point of the yarn are held in close proximity, and a portion of the yarn between the two points is of a predetermined length. A predetermined tension force is temporarily exerted to the portion of the yarn, and simultaneously the portion of the yarn is temporarily restricted from twisting when the tension force is exerted. Then the portion of the yarn is released from the tension force such that the portion of the yarn is able to twist freely so as to form snarls thereon. Thereafter, the snarling properties of the yarn are measured by detecting an amount of the snarls thereby formed.

34 Claims, 3 Drawing Sheets

OTHER PUBLICATIONS

Bennett et al., Jour of Textile Institute, vol. 4, 1974, pp. 133-141, A Study of Yarn Torque and its Dependence on the . . . .

Noor, Textile Asia, No. 11, 1993, pp. 50-55, Torsional characteristics of fibrous strands.

Morton et al, Jour of Textile Institute, vol. 38, 1947, pp. 54-59, The Measurement of Torsional Relaxation Textile Fibres.

Tavanai et al, Jour of Textile Institute, vol. 87, 1996, pp. 50-58, Direct Objective Measurement of Yarn-torque Level.

International Standard 3343-1984(E), Textile glass—Yarns—Determination of twist balance index.

Primentas, Indian Jour of Fibre & Textile Res, vol. 28, Mar. 2003, pp. 23-28, Direct determination of yarn snarliness.

* cited by examiner

YARN SNARLING TESTING APPARATUS AND METHOD

BACKGROUND

1. Field of the Invention

The present invention relates to textile technologies, and more particularly to methods and apparatus for testing snarling properties of yarns or the like.

2. Background of the Invention

In almost all types of spun yarns there exists some residual torque, which makes these yarns prone to snarling. Snarls are formed when two ends of a twist lively yarn are brought together. Yarn snarling has a significant influence on the processing behavior and performance characteristics of yarns and fabrics. In textile technological processes snarling caused by residual torque is considered as a serious problem leading to yarn breakage, deterioration of yarn properties and equipment malfunction. Fabric characteristics such as spirality of knitted fabrics and skewness of woven fabrics are also dependent on the level of residual torque in a yarn. Thus the measurement of yarn residual torque is particularly important.

Despite its importance as a yarn quality parameter, the measurement of yarn residual torque is actually rarely used to characterize a twisted yarn.

Although there has never been a generally available standard instrument for measuring the torsional characteristics of textile fibers or yarns, various methods and apparatus have been developed and can be divided into three categories, namely direct, semi-direct or indirect measurements.

Two experimental techniques to measure yarn torque by using the direct method, namely torsion pendulum and torsion balance techniques have been reported by Dhingra and Postle in the Journal of the Textile Institute, Vol. 65, 1974. According to Dhingra and Postle, the torsion pendulum technique is simple and rapid and does not require any elaborate apparatus but the information provided is severely limited in that the rigidity is measured for only small strains, imposed for a short period of time. This technique is not suitable for investigation of the torsional behavior of twisted yarns owing to the untwisting tendency of the lower end of the yarn. The torsion balance technique involves attaching one end of a twist lively yarn of specified length to a torsion disc, with the other end fixed. The torsion disc is attached to a torsion wire of known torsional stiffness. A pointer or similar indicating device is positioned between the specimen and the torsion wire. As the specimen is twisted, the torsion wire head is rotated manually so as to maintain the pointer freely in a constant position or, alternatively, the head may be fixed and the torque measured by the rotation of the indication device.

In the Journal of the Textile Institute, Vol. 4, 1979 Bennett et al used a torsion balance to experimentally measure yarn torque to investigate the torque-twist and recovery characteristics of continuous-filament and staple-fiber yarns. A torsional apparatus has been described by Noor in Textile Asia, No. 11, 1993. The apparatus consists of a twisting unit, a torque-measuring unit, a contraction measuring unit and associated data recording devices. Morton and Permanyer in the Journal of the Textile Institute, Vol. 38, 1947 disclosed the details of a device to measure the torsional rigidity of textile fibers called a Torsiometer. The Torsiometer consists of three parts arranged in vertical alignment: at the top a measuring head; at the bottom a twisting unit; and between them a rigid connecting link carrying an equilibrium pointer.

Tavanai et al reported a semi-direct method to measure yarn-torque level in the Journal of the Textile Institute, Vol. 87, 1996 called the Torquemeter. The method involves free rotation of a disc "attached to one end of a vertically suspended twist-lively yarn, with the upper end fixed, the disc will rotate and oscillate back and forth until it finally comes to rest." The system to evaluate the twist liveliness can be measured by one of two approaches: the first one being the total number of turns of twist change by the difference between the sum of forward and backward rotations A second approach disclosed by Berndt et al in Melliand Textilberichte, No. 65, 1984 uses a specially designed disc containing holes arranged in a binary pattern "which allows infra red senders and receivers to detect the direction of yarn twist liveliness and the number and rate of yarn and disc rotation. The torque in the yarn can be computed from the oscillation data and other constants, such as disc inertia."

The indirect method as described in the ISO Standard 03343-1984, is one of the simplest ways to obtain an idea about the residual torque in yarns by counting the number of snarls in a 1 m yarn segment with the two ends completely in contact. Based on the principle that a yarn containing residual torque will tend to snarl, several attempts have been made to develop a method to measure yarn snarliness. These methods usually involve suspending a light object from the middle of a known length of yarn. As soon as the two ends are brought together, snarls are formed. The number of turns or the distance between the two yarn ends when a snarl begins to form gives the snarliness level. Primentas disclosed the details of a device for testing yarn snarliness called 'Prianic' in The Indian Textile Journal, Vol. 28 No. 3, 2003. However, the method of measuring the twist liveliness by measuring the distance when a snarl begins to form can be, in practice, difficult to determine the exact point of snarling if the yarn is very twist lively.

Although a number of direct, semi direct and indirect methods of yarn residual torque evaluation exists, the most accurate method can be considered to be the direct approach. However this method may not be industrially practical since that elaborate and complex apparatus is required and that the results obtained by different authors are not easily comparable because of the different types of apparatus used and the different conditions under which the experiments were performed.

OBJECT OF THE INVENTION

Therefore, it is an object of the present invention to provide a more accurate method and apparatus, which indirectly measure the snarling properties of the yarn, or at least provide the public with a useful choice.

SUMMARY OF THE INVENTION

According to an aspect of present invention, in a process for measuring snarling properties of a yarn, firstly a first and a second point of the yarn are held in close proximity, and the portion of the yarn between the two points is of a predetermined length. A predetermined tension force is temporarily exerted to the portion of the yarn, and simultaneously the portion of the yarn is temporarily restricted from twisting when the tension force is exerted. Then the portion of the yarn is released from the tension force such that the portion of the yarn is able to twist freely so as to form snarls thereon. Thereafter, the snarling properties of the yarn are measured by detecting an amount of the snarls thereby formed.

According to another aspect of the present invention, a yarn snarling measurement system for measuring snarling properties of a yarn includes at least one holding means for holding a first and a second point of the yarn in close proximity, wherein a portion of the yarn between the two points is of a predetermined length; and means, located in close proximity to a position through which said portion of the yarn extends, for temporarily exerting a predetermined tension force to said portion of the yarn and for temporarily restricting said portion of the yarn from twisting when the tension force is exerted on the yarn, a release means to release said tension force, wherein upon release of the tension force from the yarn, said portion of the yarn is able to twist freely so as to form snarls thereon such that the snarling properties of the yarn can be measured by detecting an amount of the snarls thereby formed.

Other aspects and advantages of the invention will become apparent from the following detailed description, taken in conjunction with the accompanying drawings, which description illustrates by way of example the principles of the invention.

DETAILED DESCRIPTION

Figure 1:
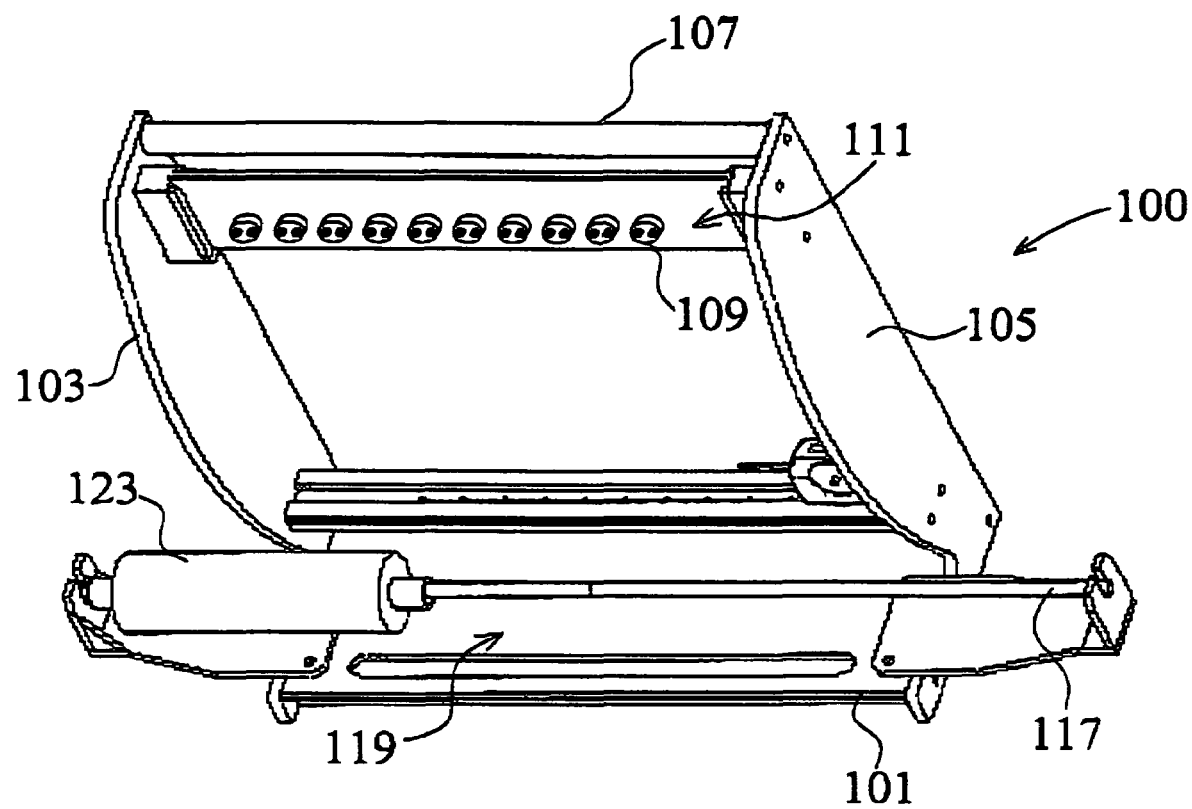
FIG. 1 is a perspective view of a yarn snarling measurement system in accordance with an exemplary embodiment of the present invention.

As shown in FIG. 1, a yarn snarling measurement system 100 in accordance with an exemplary embodiment of the present invention has a frame 101 with a pair of sidewalls 103, 105 at least substantially parallel to each other. A supporting frame 107 connects and extends at least substantially perpendicular to the sidewalls 103, 105. In operation, both the sidewalls 103, 105 and the back wall 107 extend at least substantially vertically.

At least one clamper 109 is mounted to an upper side 111 of the back wall 107, and a tension meter 113 is located away from the clamper 109 at a predetermined distance. The tension meter 113 has an extension 115, which in the exemplary embodiment extends at least substantially perpendicular to the sidewalls 103, 105.

In the exemplary embodiment, the frame 101 also has a rod 117 located adjacent the bottom side 119 and extending at least substantially perpendicular to the sidewalls 103, 105. In the exemplary embodiment, the rod 117 acts as a package holder with yarns 123 wound thereon.

The present invention indirectly measures the snarling properties of the yarns 123 by counting an amount of the snarls (not shown) formed on a sample yarn 201 of a predetermined length as illustrated in detail below in the exemplary process.

Figure 2:
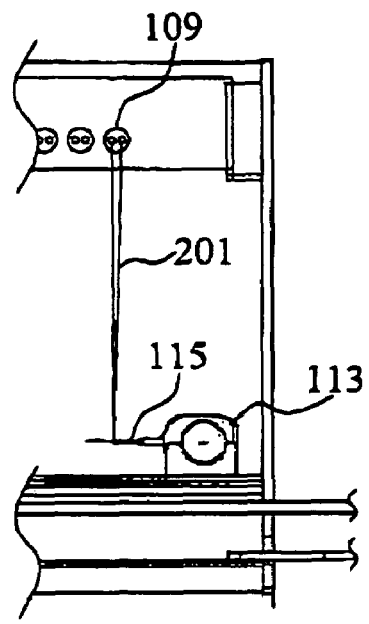
FIG. 2 is a partial front elevation view of the system of FIG. 1, with a yarn in a process of snarling measurement.

In operation, as shown in FIG. 2, the tension meter 113 is vertically aligned with the clamper or yarn holding means 109 and spaced at a predetermined distance from the clamper 109. The clamper 109 clamps one end of a selected sample yarn 201 of a predetermined length, which is approximately twice of the predetermined distance between the tension meter 113 and the clamper 109. The yarn 201 passes through the extension 115 of the tension meter 113, with the other end also clamped by clamper 109 such that the two ends are held in close proximity. The tension meter 113 is adjusted to exert a predetermined tension force onto the yarn 201 to straighten the sample yarn 201 in order to accurately ensure that the sample yarn 201 is of a predetermined length between the two ends without snarls formed thereon.

In the exemplary embodiment, the length of the sample yarn 201 between the two ends is in the range of 50–100 centimeters. The amount of predetermined tension force is such that it is sufficient to remove the yarn snarls but not too great to cause the yarn 201 to extend so as to affect the internal structure of the yarn. Such a tension force is mainly dependent upon the length and material of the sample yarn 201. In the exemplary embodiment, in which the yarn 123 is 100% cotton, the value of the tension force is set be approximately 0.06 CN/tex.

Afterwards, the yarn 201 is released from the tension meter 113 manually such that the yarn 201 can twist or rotate itself freely due to its internal strains or torsions while still retained by means 109. Thereby, snarls (now shown) will be formed on the yarn 201. When this process is finished, that is, the sample yarn 201 has fully released its internal torsion torque or strain, the yarn 201 stops twisting. Thereafter, the snarling properties of the yarn 201 can be measured by counting an amount of the snarls, for example, by using a twist tester to untwist the yarn so as to remove all the snarls.

Figure 3:
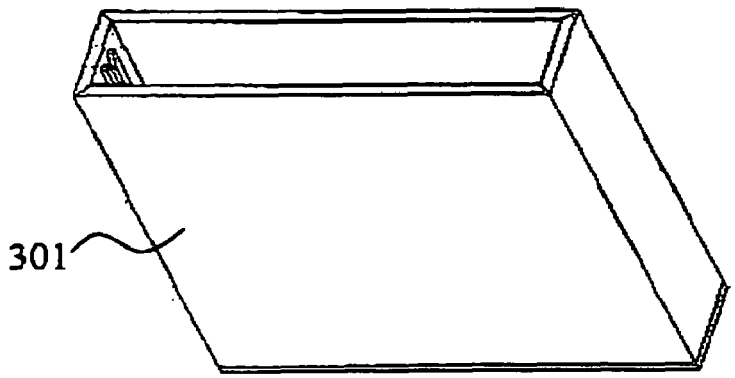
FIG. 3 is a perspective view of a water bath, which can be used in the system of FIG. 1.

In the exemplary embodiment, the yarn (not shown in FIG. 3) is immersed into liquid such as water (not shown) in the exemplar embodiment contained in a water bath 301 of FIG. 3 after it is released from the tension meter, and twists itself in the water to form the yarns. Immersion of the yarn into the water helps to accelerate the release of the internal strain of the yarn.

A dead weight such as a hook (not shown) is loaded to the yarn before the yarn is immersed into the water to ensure the yarn is fully immersed into the water and does not float on the surface of the water. The optimum dead weight is determined experimentally, dependent upon the linear density and material of the yarn, so as to not restrict the twist or rotation of the yarn in the water. In the exemplary embodiment, it is ascertained that a dead weight between 0.003 CN/tex and 0.01 CN/tex is preferred.

Figure 4A:
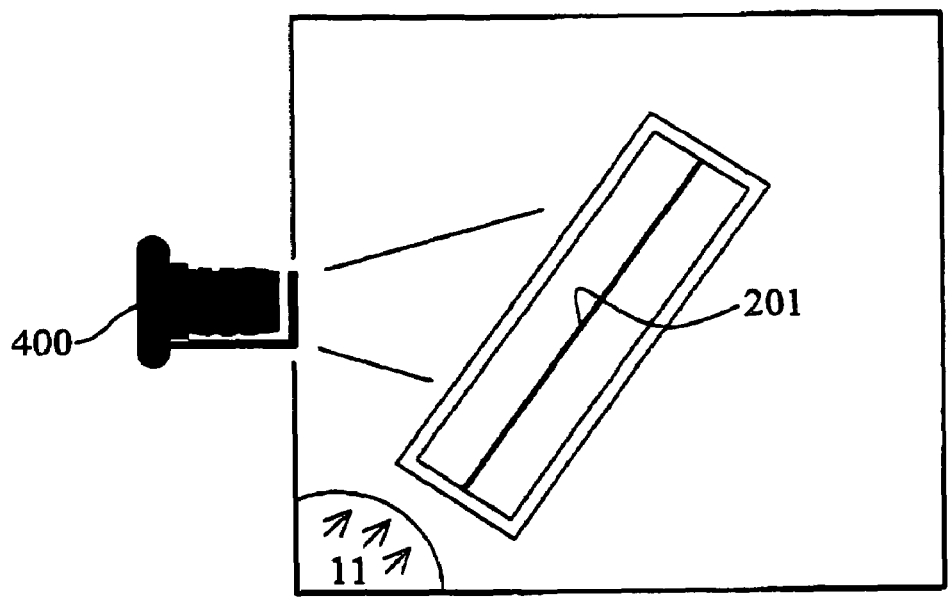
FIG. 4A illustrates part of an image processing system which can be used in the system of FIG. 1.
Figure 4B:
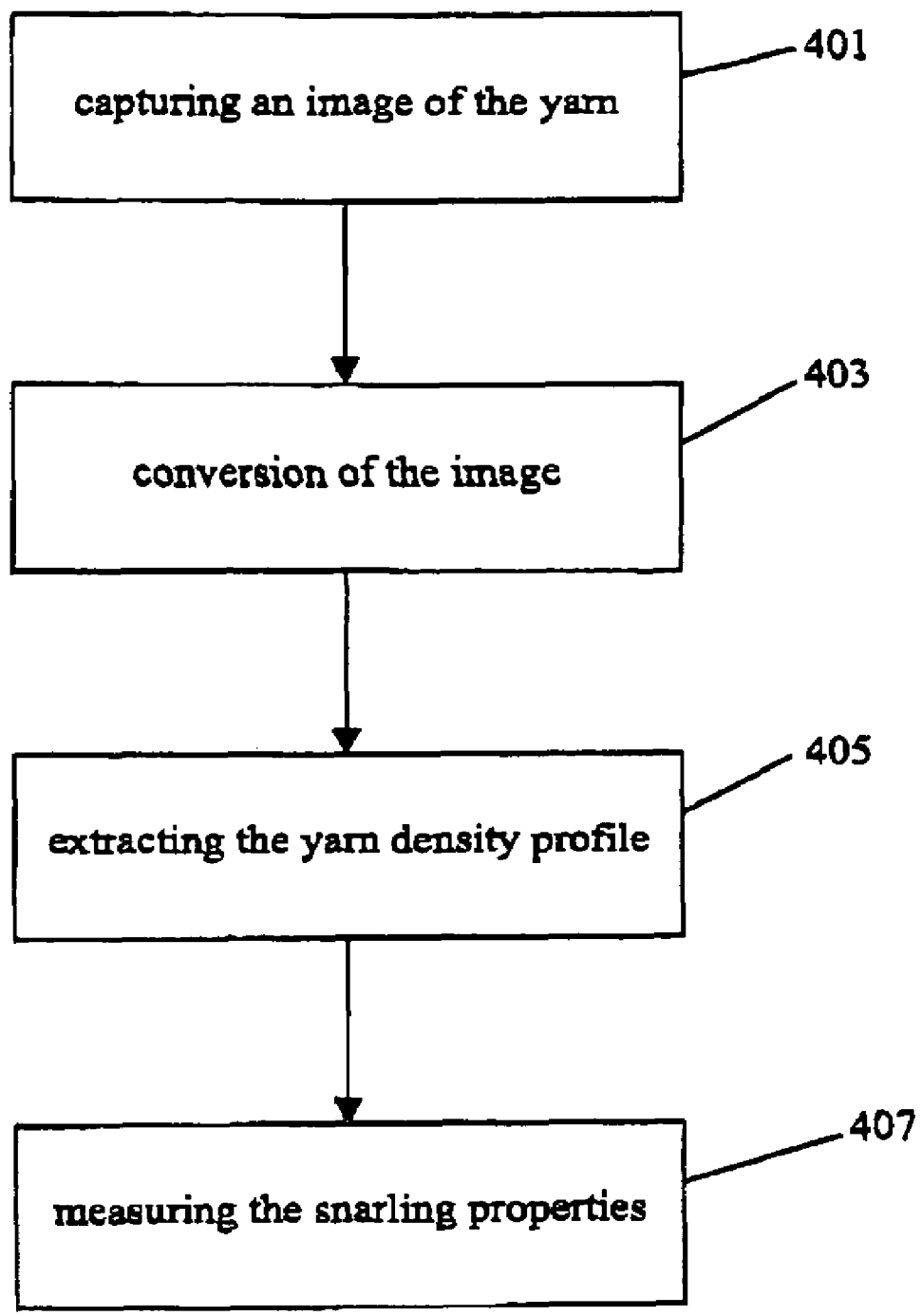
FIG. 4B is a flow chart illustrating part of yarn snarling measurement system in accordance with an exemplary embodiment of the present invention.

Furthermore, in the exemplary embodiment, an image processing process is used to detect the amount of snarls formed on the sample yarn as described with reference to FIGS. 4A and 4B.

In step 401, firstly, an image capturing device 400 is used to capture an image of the sample yarn after the sample yarn has fully released its internal strain and the yarn has stopped twisting. Then the captured image is converted to a greyscale image and further to a binary image in step 403 for further digital processing. In step 405, a feature called yarn density profile, which is defined as yarn cross-sectional width along its length, is extracted from the binary image. Based on this yarn density profile, in step 407, the amount of the snarls formed on the sample yarn and further the snarling properties of the yarn can be measured. Specifically, in step 407, The Fast Fourier Transform (FFT) and the Adaptive Oriented Orthogonal Projective Decomposition (AOP) functions are combined to simulate and count the yarn snarls automatically and precisely. In the FFT processing, the yarn density profile is treated as one section of one-dimensional signal, and the fluctuation cycle of yarn density profile caused by yarn snarling can be approximately determined by calculating the corresponding frequency component. Finally the approximate fluctuation cycle will be used as the input to the following AOP processing, wherein all fluctuations in yarn density profile caused by its snarling can be accurately simulated by the Gauss-functions of different character parameters, and the number of Gauss-functions used for the simulation indicates the number of the yarn snarls.

Alternatives can be made to the exemplary embodiment. For example, more than one clamper can be used to hold the two ends of the sample yarn in close proximity. The tension meter can be replaced with a dead weight for exerting the predetermined tension force. In addition, a heating or cooling element can be used to vary the temperature of the liquid so as to test the yarn snarling properties at different temperatures.

What is claimed is:

1. A process for measuring snarling properties of a yarn, said process comprising:
   holding a first and a second point of a yarn, wherein a portion of the yarn between the two points is of a predetermined length;
   exerting a predetermined tension force to said portion of the yarn and restricting said portion of the yarn from twisting during exertion of the tension force;
   releasing the tension force from the yarn and allowing said portion of the yarn to twist freely so as to form snarls thereon; and
   measuring the snarling properties of the yarn by determining a number of the snarls thereby formed.

2. The process of claim 1, wherein the tension force is applied between a middle of said portion of the yarn and the first and second points, such that said portion of yarn is divided into two portions of a substantially equal length aligned substantially parallel and in close proximity to each other.

3. The process of claim 1, further comprising
   selecting the tension force dependent upon a characteristic of the yarn.

4. The process of claim 1, further comprising
   capturing an image of the twisted yarn with snarls formed thereon for further processing to determine the number of the snarls.

5. The process of claim 4, further comprising
   extracting a density profile of said portion of the yarn from the captured image; and
   determining the number of the snarls based upon the density profile.

6. The process of claim 5, further comprising
   converting the captured image into a format suitable for digital processing.

7. The process of claim 1, further comprising
   immersing at least part of said portion of the yarn into a liquid when allowing said portion of the yarn to twist freely after release of the tension force.

8. The process of claim 7, further comprising varying temperature of the liquid.

9. A yarn snarling measurement system for measuring snarling properties of a yarn, the system comprising
   at least one holding means for holding a first and a second point of a yarn, wherein the portion of the yarn between the two points is of a predetermined length;
   means, for exerting a predetermined tension force to said portion of the yarn and for restricting said portion of the yarn from twisting during exertion of the tension force;
   wherein upon release of the tension force from the yarn, said portion of the yarn is able to twist freely so as to form snarls thereon such that the snarling properties of the yarn can be measured by determining a number of the snarls thereby formed.

10. The system of claim 9, wherein said means is a tension meter positionable at an intermediate point of said portion of the yarn such that said portion is divided into two substantially parallel portions in close proximity to each other.

11. The system of claim 9, wherein said means is a dead weight attached to an intermediate point of said portion of the yarn such that said portion is divided into two substantially parallel portions in close proximity to each other.

12. The system of claim 9, wherein the predetermined tension force is selected upon a characteristic of the yarn to be determined.

13. The system of claim 9, wherein the means is adapted to draw the yarn longitudinally under the predetermined tension force.

14. The system of claim 9, further comprising an image processing apparatus for capturing an image of the twisted portion of the yarn with the snarls formed thereon.

15. The system of claim 14, wherein the image processing apparatus includes
   an image extractor for extracting a density profile of said portion of the yarn from the captured image; and
   a processor for detecting the number of the snarls based upon the density profile.

16. The system of claim 15, wherein the image processing apparatus further includes
   a converter for converting the captured image into a format suitable for processing by the image extractor.

17. The system of claim 15, wherein the processor of the image processing apparatus detects the number of the snarls by simulating the snarls of said portion of the yarn.

18. The system of claim 17, wherein the processor detects the amount of the snarls by using East Fourier Transform and Adaptive Oriented Orthogonal Projective Decomposition to simulate and count the snarls of said portion of the yarn.

19. The system of claim 9, further comprising
   a container for holding a liquid therein and for receiving at least part of said portion of the yarn and allowing immersion of said portion of the yarn during release of the tension force.

20. The system of claim 19, further comprising a heater for varying temperature of the liquid.

21. The system of claim 19, further comprising a cooler for varying temperature of the liquid.

22. A process for measuring snarling properties of a yarn, said process comprising the steps of:
   applying a tensile load to a predefined length of yarn whilst preventing the yarn from twisting;
   releasing the tensile load and allowing the yarn to twist and there by form a number of snarls; and
   determining the number of snarls formed by the yarn;
   wherein the numbers of snarls formed is indicative of the snarling properties of the yarn.

23. The process of claim 22, wherein the tensile load is applied to the yarn such that the yarn assumes a configuration whereby the length is divided into two portions whereby the portions are substantially axially aligned.

24. The process of claim 22, wherein the tensile load is applied between the center of the length of yarn and the end portions of the length of yarn, such that the yarn assumes a configuration whereby the length is divided into two portions whereby the portions are substantially axially aligned.

25. A process for measuring snarling properties of a yarn, said process comprising:
holding a first and a second point of the yarn in close proximity, wherein a portion of the yarn between the two points is of a predetermined length;
temporarily exerting a predetermined tension force to said portion of the yarn, and simultaneously temporarily restricting said portion of the yarn from twisting when the tension force is exerted on the yarn;
releasing the yarn from the tension force such that said portion of the yarn is able to twist freely so as to form snarls thereon;
measuring the snarling properties of the yarn by detecting an amount of the snarls thereby formed; and
immersing at least part of said portion of the yarn into liquid alter release of the tension force, where the yarn twists freely.

26. The process of claim 25, further comprising varying temperature of the liquid.

27. A yarn snarling measurement system for measuring snarling properties of a yarn, said system comprising
at least one holding means for holding a first and a second point of the yarn in close proximity, wherein a portion of the yarn between the two points is of a predetermined length;
means, located in close proximity to a position through which said portion of the yarn extends, for temporarily exerting a predetermined tension force to said portion of the yarn and for temporarily restricting said portion of the yarn from twisting when the tension force is exerted on the yarn,
release means for releasing said tension force, wherein upon release of the tension force from the yarn, said portion of the yarn is able to twist freely so as to form snarls thereon such that the snarling properties of the yarn can be measured by detecting an amount of the snarls thereby formed,
an image processing apparatus in close proximity to said portion of the yarn for capturing an image of the twisted portion of the yarn wit the snarls formed thereon.

28. The system of claim 27, wherein the image processing apparatus includes
an image extractor for extracting a density profile of said portion of the yarn from the captured image; and
a processor for detecting the amount of the snarls based upon the density profile.

29. The system of claim 28, wherein the image processing apparatus further includes
a converter for converting the captured image into a format suitable for processing by the image extractor.

30. The system of claim 28, wherein the processor of the image processing apparatus detects the amount of the snarls by simulating the snarls of said portion of the yarn.

31. The system of claim 30, wherein the processor detects the amount of the yarns by using Fast Fourier Transform and Adaptive Oriented Orthogonal Projective Decomposition to simulate and count the snarls of said portion of the yarn.

32. A yarn snarling measurement system for measuring snarling properties of a yarn, said system comprising
at least one holding means for holding a first and a second point of the yarn in close proximity, wherein a portion of the yarn between the two points is of a predetermined length;
means, located in close proximity to a position through which said portion of the yarn extends, for temporarily exerting a predetermined tension force to said portion of the yarn and for temporarily restricting said portion of the yarn from twisting when the tension force is exerted on the yarn,
release means for releasing said tension force, wherein upon release of the tension force from the yarn, said portion of the yarn is able to twist freely so as to form snarls thereon such that the snarling properties of the yarn can be measured by detecting an amount of the snarls thereby formed,
a container with liquids therein, wherein at least part of said portion of the yarn is immersed into the liquid after release of the tension force and twists freely in the liquid to form snarls.

33. The system of claim 32, further comprising a heater coupled to the container for varying temperature of the liquid.

34. The system of claim 32, further comprising a cooler coupled to the container for varying temperature of the liquid.

* * * * *